United States Patent [19]

Pugliese

[11] 4,398,541
[45] Aug. 16, 1983

[54] METHOD AND APPARATUS FOR MEASURING MOISTURE CONTENT OF SKIN

[75] Inventor: Peter Pugliese, Bernville, Pa.

[73] Assignee: Xienta, Inc., Bernville, Pa.

[21] Appl. No.: 909,664

[22] Filed: May 25, 1978

[51] Int. Cl.$^3$ .............................................. A61B 5/00
[52] U.S. Cl. ................................................... 128/665
[58] Field of Search ............ 128/2 A, 2 R, 2 W, 2 L, 128/2.1 R, 665–667, 630, 633; 73/73, 335–336; 356/364–370, 335–337; 5/451

[56] References Cited

U.S. PATENT DOCUMENTS

| | | | |
|---|---|---|---|
| 3,205,355 | 9/1965 | Ehlert | 73/73 |
| 3,283,644 | 11/1966 | Saltzman | 356/367 X |
| 3,355,980 | 12/1967 | Mathias | 356/369 |
| 3,525,803 | 8/1970 | Smart | 356/367 |
| 3,572,938 | 3/1971 | Bradford | 356/367 |
| 3,612,689 | 10/1971 | Liskowitz | 356/364 X |
| 4,015,127 | 3/1977 | Sharkins | 356/369 |

OTHER PUBLICATIONS

Biedermann, E., "Measuring the Thickness of Thin Transparent Films", IBM Tech. Discl. Bulletin, vol. 14, No. 3, Aug. 1971, pp. 967–968.

Primary Examiner—Kyle L. Howell
Assistant Examiner—Francis J. Jaworski
Attorney, Agent, or Firm—Gottlieb, Rackman & Reisman

[57] ABSTRACT

There are disclosed a method and an apparatus for measuring moisture content of skin. The skin surface is illuminated with polarized light incident at the Brewster angle. The degree of polarization of the light refracted within the skin and reflected out is measured. The measurement is a function of the refractive index of the skin which, in turn, is a function of the moisture content. To avoid measurement variations due to such things as skin color, output readings are in the form of a ratio of the reflected polarized light intensity to the reflected total light intensity.

27 Claims, 1 Drawing Figure

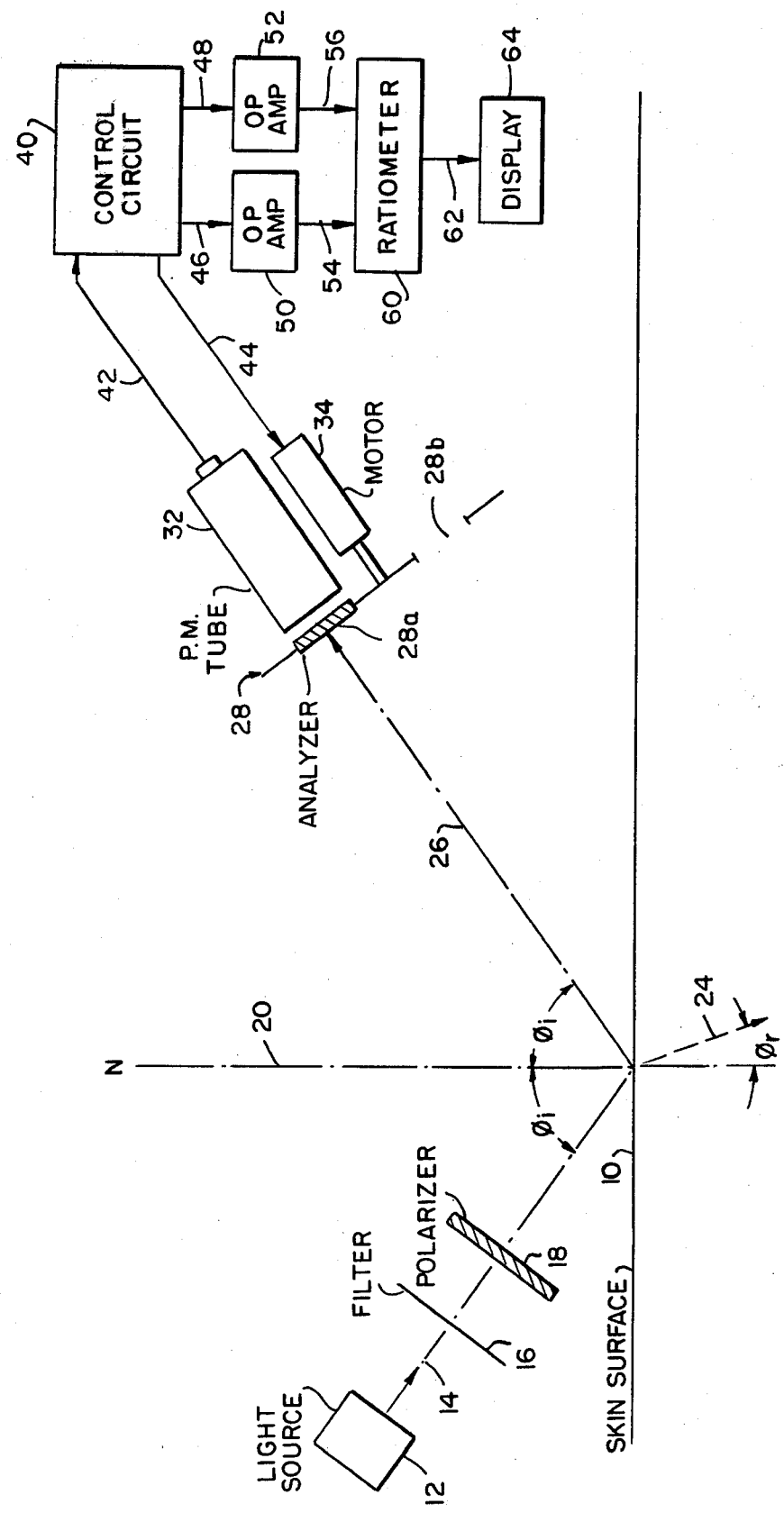

METHOD AND APPARATUS FOR MEASURING MOISTURE CONTENT OF SKIN

This invention relates to a method and an apparatus for measuring the moisture content of skin, and more particularly to the taking of in vivo measurements in a rapid, simple and accurate manner.

The medical profession and the cosmetic industry have long sought a practical instrument which is capable of measuring skin moisture content in a rapid and simple manner, and with a degree of precision. Prior art attempts to provide such an instrument have not been successful. One prior art technique for measuring skin moisture content, based upon a capacitance effect, is disclosed in Copeland et al U.S. Pat. No. 4,013,065, entitled "Moisture Dermatometer," which issued on Mar. 22, 1977.

Light has also been used in the prior art to measure skin characteristics. In DeWitt et al U.S. Pat. No. 4,029,085, entitled "Method for Determining Bilirubin Concentration from Skin Reflectance," which issued on June 14, 1977, there is disclosed a technique for measuring the spectral reflectance of skin to determine bilirubin concentration. This technique entails the illumination of the skin at different wavelengths, and measuring the intensity of the reflected light at each wavelength. But the technique is not applicable for determining the moisture content of skin.

It is also known in the prior art to use polarized light for taking measurements of different kinds. For example, in Gee U.S. Pat. No. 3,904,293, entitled "Optical Method for Surface Texture Measurement," which issued on Sept. 9, 1975, there is disclosed a method for measuring the textural characteristics of a surface by illuminating the surface with polarized light and measuring the degree of depolarization of the reflected light. The use of polarized light transmitted through an object of interest for comparing one pattern with another is disclosed in Green et al U.S. Pat. No. 3,982,836, entitled "Method and Means for Enhancing Prints for Direct Comparison," which issued on Dec. 28, 1976. Of perhaps greater interest to the subject invention are Aspnes U.S. Pat. No. 3,985,447, entitled "Measurement of Thin Films by Polarized Light," which issued on Oct. 12, 1976, and Dill et al U.S. Pat. No. 4,053,232, entitled "Rotating-Compensator Ellipsometer," which issued on Oct. 11, 1977. In both of these patents, there are disclosed techniques for using polarized light to measure the thickness and/or refractive index of a thin film. But these patents do not suggest the use of polarized light to measure the moisture content of skin.

Even should it be thought that light (e.g., polarized) might be used to measure moisture content of skin, there is a logical reason for rejecting such an attempt. It is apparent that the intensity of the light which is reflected from the human skin necessarily depends on its texture and color. Since there is a wide range of skin color, it would appear that it would not be feasible to relate the intensity of the reflected light to moisture content (even assuming that, quite apart from skin color effects, the reflected light intensity is somehow a function of moisture content).

The scientific basis for my invention is predicated upon the following principles of optical physics. A ray of unpolarized light which is incident on an object is separated into a reflected ray and a refracted ray. With respect to the reflected ray, the angle of reflection equals the angle of incidence. The angle of the refracted ray is determined by the well-known Snell's Law. A special case, covered by Brewster's Law, is that in which the angle of incidence (to a line normal to the surface) is the Brewster angle (about 57° for ordinary glass). In such a case, it is found that the reflected light, while being only a small fraction of the total incident light, is plane-polarized. Furthermore, the reflected and refracted rays are 90° apart. It is also well known that the intensity of the reflected plane-polarized light can be increased by stacking a pile of glass plates one on top of the other. The refracted ray in the top plate is partially reflected (plane-polarized) from the bottom surface of the plate. As the unreflected part of the ray moves on to the upper surface of the second plate, part of it is reflected (plane-polarized). This process continues as the reflected ray, which gets lower and lower in intensity, is partially reflected at both surfaces of each plate. All of the reflected rays are plane-polarized and parallel with the plane-polarized ray reflected from the uppermost plate surface. The net result is that the composite ray reflected from the pile of plates (at a reflection angle which equals the angle of incidence) is not only plane-polarized, but can also have an intensity which is an appreciable fraction of the intensity of the incident unpolarized light. These effects are described, for example, in Jenkins and White, "Fundamentals of Optics," McGraw-Hill Book Company, Inc., 1957, pages 488–494.

The skin consists of epidermis and dermis as the two major divisions. The epidermis is a transparent structure that may be structurally divided into four layers. The outer layer is the stratum corneum, the second layer is the granular layer, the third layer is called the prickle layer, and the lowest layer is known as the basement membrane. Each of these layers has a distinct cellular structure. Since the epidermis consists of layers of transparent cells, light passing through the epidermis may be treated in the same manner as light passing through a pile of parallel glass plates. Unpolarized light striking the epidermal surface at the Brewster angle will be mostly transmitted through the epidermis and thus refracted. Some of the vibrations perpendicular to the plane of incidence are reflected (plane-polarized) at each surface, and all of the vibrations parallel to the plane of incidence are refracted. The net result is that the reflected rays are all plane-polarized in the same plane, and the refracted beam having lost most of the perpendicular components of vibration is partially polarized in the other plane.

In the case of a stack of glass plates, the degree of polarization of the reflected light is a function of both the number of plates in the stack and their refractive index (see, e.g., page 493 of the Jenkins and White text). Consequently, since the skin affects incident light as does a pile of parallel glass plates, the degree of polarization of the reflected light is a function of the refractive index of the skin.

The refractive indices of many biological fluids are functions of their concentrations of proteins and salts. The concentration of any biological fluid is inversely related to the water content in that fluid matrix. Therefore, if unpolarized light is incident upon a skin surface, the degree of polarization of the reflected light is necessarily a function of the refractive index of the skin which, in turn, is a function of the moisture content of the skin. The underlying technique of my invention is to direct a ray of light toward the skin surface, and to measure the degree of polarization of the reflected light to determine the moisture content of the skin.

There are two refinements of this basic technique, however, which make it both practical and accurate, and are incorporated in the preferred embodiment of the invention. The first refinement concerns the use of an incident beam of light which is polarized rather than unpolarized, and which impinges on the skin at approximately the Brewster angle (within the range 45°-60° incident to the normal, with an angle of 54° being preferred). When unpolarized light is used, it is found that the degree of polarization of the reflected light is a function of the moisture content of the skin, but even large variations in moisture content result in relatively small variations in the degree of polarization. In other words, any instrument which uses unpolarized light has a small dynamic range which can lead to inaccurate results. But when polarized light is used, and especially when it is incident at approximately the Brewster angle (45°-60° to the normal, with 54° being preferred), there are large variations in the degree of polarization of the reflected light depending on the skin moisture content. The light which is reflected from the upper surface of the skin is scattered due to the non-smooth texture of the skin. While this portion of the reflected light is partially polarized, since only a small part of the scattered light is detected it does not affect the overall measurement to a significant degree (as is desired inasmuch as the light reflected from the upper skin surface is not a function of moisture content). It is the light which is refracted and then reflected within the skin whose intensity varies greatly with the moisture content. Thus the use of polarized light incident at the Brewster angle is clearly preferred because it provides a much wider dynamic range.

The second refinement takes into account measurement variations which would otherwise arise from such things as skin textures and especially skin colors of different patients. Considering skin color, for example, it is apparent that the total light which is internally refracted and reflected necessarily depends upon the degree to which the incident light is absorbed in the skin and this, in turn, depends on the skin color. An instrument which is calibrated to provide moisture content readings as a function of the intensity of the reflected light could not service the general population, because the calibration would be accurate only for patients having more or less the same skin color.

For this reason, the output readings of the instrument of the preferred embodiment of my invention are not simply a direct function of the degree of polarization of the reflected light. Two measurements are actually taken for each patient. The first is the intensity of the polarized light in the reflected beam. The second is the total intensity of the reflected beam. (The two measurements can be taken simply by inserting and then removing an analyzer in the path of the reflected light, as is known in the art.) The output measurement is proportional to the ratio of the first reading to the second. Skin texture and color, as well as other variables, affect both readings to approximately the same degree. Thus, both measurements for one patient may be just half of both respective measurements for another, but the ratio of measurements for both patients will be the same if they have equal skin moisture contents. It must be understood that the "normalization" introduced by taking ratio measurements is not a normalization which is the same for all patients; the denominator is not a constant for all patients. On the contrary, the normalization is different for each patient in that any measurement of reflected polarized light intensity is normalized relative to the reflected total light intensity for the same patient. The instrument may be calibrated in terms of ratio measurements versus average moisture content determinations (using standard accurate, albeit expensive and time-consuming, techniques) for a large population; the ratio measurement for each patient subsequently tested can thus be compared with a standard "ratio versus moisture content" curve to determine the skin moisture content of the patient, without any regard being given to other skin variables which might otherwise render the measurement inaccurate.

Further objects, features and advantages of my invention will become apparent upon consideration of the following detailed description in conjunction with the drawing which depicts a preferred embodiment of the invention.

Referring to the drawing, light source 12, which may be a source of unpolarized light, directs a beam of light 14 through filter 16 and polarizer 18 to the skin surface 10. The filter is designed to provide a relatively narrow bandwidth (preferably, 5-10 nanometers) of wavelengths, although it is not essential to the practice of the invention. The preferred wavelengths are those which are not absorbed by the skin so that a maximum amount of light may be reflected from the skin. Also, since the refractive index of any material is, to at least a small degree, dependent upon the wavelength of radiation, it is preferable to use a narrow band of wavelengths. In general, the entire range of wavelengths from 450 nanometers to 700 nanometers has been found to be practical, although wavelengths centered as closely as possible to 700 nanometers are preferred. (The greater the intensity of the light source, the narrower may be the wavelength bandwidth; what is necessary, of course, is to have a total quantity of incident light which allows measurements to be taken on the reflected light.) A conventional polarizer 18 is utilized in order to polarize the light which is incident on the skin surface.

The light is incident at an angle $\phi_i$ to the normal N. The reflected light 26 is at the same angle $\phi_i$ to the normal, and the refracted light 24 within the skin is at an angle $\phi_r$ to the normal. As described above, the refracted light undergoes numerous reflections within the skin, all of the reflected rays exiting the skin surface in a direction parallel with ray 26.

A disc 28 is provided with two apertures. Aperture 28b is clear, while a conventional analyzer 28a is placed in the other aperture. The analyzer is oriented to pass light which is plane-polarized in the orientation of beam 14. (The final reading displayed thus increases with the degree to which the polarization of reflected beam 26 increases as a function of skin moisture content.) The disc is turned by motor 34 so that the reflected light 26 passes through analyzer 28a on its way to photomultiplier tube 32 when the disc is in the position shown in the drawing, or the light simply passes through aperture 28b when the motor has rotated the disc 180°. In either case, the output of the photomultiplier tube on conductor 42 is extended to control circuit 40.

The signal on conductor 42 is extended by the control circuit over either conductor 46 or conductor 48 to one of respective operational amplifiers 50 and 52. The amplified signals are extended over conductors 54 and 56 to a conventional ratiometer 60 which forms the ratio of the two signals on the respective input conductors, and applies a signal proportional to the ratio over conductor 62 to the input of any conventional display unit 64 which then displays the result.

Control circuit 40 first extends a signal over conductor 44 to motor 34 which controls the rotation of disc 28 so that aperture 28b is in front of the photomultiplier tube 32. The resulting "normalizing" (denominator) signal on conductor 42 is extended by the control circuit over conductor 46 to operational amplifier 50. Thereafter, the control circuit extends a signal over conductor 44 to cause the motor to rotate disc 28 180° (to the position shown in the drawing). The resulting "degree of polarization" signal on conductor 42 is now extended by the control circuit over conductor 48 to operational amplifier 52. The only function of the control circuit is to establish a connection between conductor 42 and one of conductors 46 or 48 depending upon the position of disc 28 as determined by the signal applied to conductor 44. The ratiometer then forms the ratio of the signal level on conductor 56 to the signal level on conductor 54, with the resulting ratio being displayed on display 64.

The control circuit can cause disc 28 to step continuously between its two positions so that continuous signals appear on conductors 54 and 56 to facilitate the formation of the ratio signal on conductor 62. In order to maintain the signal on each of conductors 54 and 56 while the other signal is being derived, if that is necessary for the operation of the ratiometer, the output of each operational amplifier may be provided with a conventional sample-and-hold circuit.

As described above, the angle of incidence $\phi_i$ is the angle (54° in the preferred embodiment) which gives the largest variations in the signal on conductor 48 as a function of skin moisture content. Variations in the output readings which would otherwise be caused by variables such as skin texture and color are substantially eliminated by taking a "normalized" measurement for each patient—the numerator and denominator of the ratio are both affected by approximately the same factor for each skin variable except moisture content. Thus the resulting ratio is primarily a function of moisture content only.

The instrument may be calibrated initially based upon measurements taken on excised skin samples of a large population. For each patient in this population, the wet weight of his skin sample is recorded. The instrument is then used to take a moisture content ratio reading with some arbitrary settings of the gains of the two operational amplifiers. The skin specimen is then partially dried in an oven, re-weighed, and again placed under the instrument for the taking of a second reading. This process is continued until the dry weight of the tissue is obtained. From this data, a curve may be plotted for each patient of instrument reading versus moisture content. The individual plots are then averaged so that there results an "average" plot of instrument reading versus moisture content. In order to directly relate the instrument readings to the moisture content values in absolute terms, the gains of one or both operational amplifiers may be adjusted so that each instrument reading (a ratio) actually represents the respective moisture content value. Once the gains of the operational amplifiers are determined in this manner, these gains are used for all subsequent instruments which are produced.

This assumes, however, that the calibration curve of instrument reading versus moisture content is a linear function, but the relationship is not this exact. For this reason, for greater accuracy the calibration curve itself can be used when testing any patient. The ratio which is displayed is not necessarily the exact moisture content. The ratio is simply used to consult the calibration curve from which the actual moisture content is read.

Although the invention has been described with reference to a particular embodiment, it is to be understood that this embodiment is merely illustrative of the application of the principles of the invention. For example, each ratio reading may be the ratio of the "normalizing" signal to the "degree of polarization signal," rather than the reverse. Thus it is to be understood that numerous modifications may be made in the illustrative embodiment of the invention and other arrangements may be devised without departing from the spirit and scope of the invention.

What I claim is:

1. An apparatus for performing an in vivo measurement of the moisture content of animal or human skin comprising means for directing light toward a skin surface, means for detecting the degree of polarization of the light reflected from said skin surface, and means for determining the moisture content of the skin in accordance with the detected degree of reflected light polarization.

2. An apparatus in accordance with claim 1 wherein said determining means includes means for measuring the total light reflected from said skin surface, and means for forming a ratio one of whose factors is proportional to the detected degree of reflected light polarization and the other of whose factors is proportional to the measured total reflected light.

3. An apparatus in accordance with claim 2 wherein said directed light is polarized.

4. An apparatus in accordance with claim 3 wherein said directed light is incident at approximately the Brewster angle to the normal line through the skin surface.

5. An apparatus in accordance with claim 3 wherein said directed light is incident to the normal line through the skin surface at an angle in the range 45°-60°.

6. An apparatus in accordance with claim 5 wherein the wavelengths in said directed light are in the range 450-700 nanometers.

7. An apparatus in accordance with claim 1 wherein said directed light is polarized.

8. An apparatus in accordance with claim 7 wherein said directed light is incident to the normal line through the skin surface at an angle in the range 45°-60°.

9. An apparatus in accordance with claim 8 wherein the wavelengths in said directed light are in the range 450-700 nanometers.

10. An apparatus in accordance with claim 1 wherein the wavelengths in said directed light are centered around 700 nanometers.

11. An in vivo method for measuring the moisture content of animal or human skin comprising the steps of directing light toward a skin surface, detecting the degree of polarization of the light reflected from said skin surface, and determining the moisture content of the skin in accordance with the detected degree of reflected light polarization.

12. A method in accordance with claim 1 wherein said determining step includes the sub-steps of measuring the total light reflected from said skin surface, and forming a ratio one of whose factors is proportional to the detected degree of reflected light polarization and the other of whose factors is proportional to the measured total reflected light.

13. A method in accordance with claim 12 wherein said directed light is polarized.

14. A method in accordance with claim 13 wherein said directed light is incident at approximately the Brewster angle to the normal line through the skin surface.

15. A method in accordance with claim 13 wherein said directed light is incident to the normal line through the skin surface at an angle in the range 45°–60°.

16. A method in accordance with claim 15 wherein the wavelengths in said directed light are in the range 450–700 nanometers.

17. A method in accordance with claim 11 wherein said directed light is polarized.

18. A method in accordance with claim 17 wherein said directed light is incident to the normal line through the skin surface at an angle in the range 45°–60°.

19. A method in accordance with claim 18 wherein the wavelengths in said directed light are in the range 450–700 nanometers.

20. A method in accordance with claim 11 wherein the wavelengths in said directed light are centered around 700 nanometers.

21. An in vivo method for measuring the moisture content of animal or human skin comprising the steps of directing light toward a skin surface, measuring the intensity of light reflected from said skin surface, selectively placing analyzing means in the path of said reflected light to permit the taking of a first measurement indicative of the degree of polarization of said reflected light and the taking of a second measurement indicative of the total reflected light, and determining a ratio whose two factors are said first and second measurements.

22. A method in accordance with claim 21 wherein said directed light is polarized.

23. A method in accordance with claim 22 wherein said directed light is incident at approximately the Brewster angle to the normal line through the skin surface.

24. A method in accordance with claim 22 wherein said directed light is incident to the normal line through the skin surface at an angle in the range 45°–60°.

25. A method in accordance with claim 24 wherein the wavelengths in said directed light are in the range 450–700 nanometers.

26. A method in accordance with claim 25 wherein the wavelengths in said directed light are centered around 700 nanometers.

27. A method in accordance with claim 21 wherein the wavelengths in said directed light are centered around 700 nanometers.

* * * * *